US006448466B1

(12) United States Patent
Ribeiro de Carvalho

(10) Patent No.: US 6,448,466 B1
(45) Date of Patent: Sep. 10, 2002

(54) SANITARY NAPKIN

(75) Inventor: Antonio Carlos Ribeiro de Carvalho, Sao Paulo (BR)

(73) Assignee: Johnson & Johnson Industria E Comercio LTDA (BR)

( * ) Notice: Subject to any disclaimer, the term of this patent is extended or adjusted under 35 U.S.C. 154(b) by 70 days.

(21) Appl. No.: 09/648,679

(22) Filed: Aug. 25, 2000

(30) Foreign Application Priority Data

Dec. 29, 1999 (BR) .......................................... 19903096

(51) Int. Cl.⁷ ............................................... A61F 13/15
(52) U.S. Cl. ...................... 604/378; 604/354; 604/387; 604/385.03
(58) Field of Search .............................. 604/354, 378, 604/386, 387, 389, 390, 385.03, 385.01, 385.22, 385.16

(56) References Cited

U.S. PATENT DOCUMENTS

| | | | | |
|---|---|---|---|---|
| 5,599,337 A | * | 2/1997 | Mccoy ..................... 604/385.1 |
| 5,624,421 A | * | 4/1997 | Dabi et al. ................... 604/378 |
| 5,702,375 A | * | 12/1997 | Angelillo et al. ............ 604/358 |
| 5,743,896 A | * | 4/1998 | Parker ..................... 604/385.1 |
| 5,853,401 A | * | 12/1998 | Mayer et al. ................ 604/378 |
| 5,873,869 A | * | 2/1999 | Hammons et al. ........ 604/385.1 |
| 6,160,197 A | * | 12/2000 | Lassen et al. ................ 604/358 |
| 6,171,297 B1 | * | 1/2001 | Osborn, III et al. ...... 604/385.1 |
| 6,231,556 B1 | * | 5/2001 | Osborn, III et al. ...... 604/385.1 |
| 6,296,628 B1 | * | 10/2001 | Mizutani ..................... 604/387 |
| 6,316,688 B1 | * | 11/2001 | Hammons et al. ........... 604/378 |

* cited by examiner

Primary Examiner—John G. Weiss
Assistant Examiner—Michael Bogart

(57) ABSTRACT

A sanitary napkin and particularly an intimate woman's sanitary napkin is disclosed. The sanitary napkin is provided with a conveying element, capable of conveying the flow of vaginal exudates to a central area of the sanitary napkin, thus minimizing the possibilities of side leakage. The conveying element is vertically aligned and disposed along the longitudinal axis of the sanitary napkin above the absorbent element, and being substantially laminar and orthogonal to the surface of the sanitary napkin.

17 Claims, 2 Drawing Sheets

SANITARY NAPKIN

FIELD OF THE INVENTION

The present invention is related to a sanitary napkin, particularly a woman's sanitary napkin used to collect and retain vaginal exudates, and more specifically an intimate woman's sanitary napkin provided with a conveying element.

DESCRIPTION OF THE STATE OF THE ART

As known in the art, the woman's sanitary napkins (also simply designated as napkins in the following text) are generally disposable and used to collect and retain vaginal exudates, especially menstrual blood and inter-menstrual secretions.

Usually, such napkins are comprised of a substantially elongated absorbent core, sandwiched between a top layer and a lining layer. The top layer contacts the user's pelvic area and is generally made of a previous material that does not cause any irritation to the user's skin. The purpose of the lining layer, opposite the top layer, is to prevent the fluid retained in the absorbent core from leaking into the user's clothes, being generally made of an impervious material.

The attachment of the sanitary napkin to the user's underwear is generally carried out through adhesive areas on the outer surface of the lining layer, which are adhered to the inner surface of the area in the user's panties between her thighs. In addition, as an aid to such attachment, the napkin may be provided with side wings provided with adhesive areas that are folded and releasably adhered to the outer surface of the area in the user's panties between her thighs.

An undesirable aspect concerning the napkins known in the present art is the occurrence of leaking when the napkin is not well fitted in the user's pelvic area. When such situation takes place, the evacuation of vaginal exudate can firstly reach areas near the edges instead of the central area, and therefore brings about a leakage because it cannot be promptly absorbed, and then leaks.

Still another cause of leakage during the use of conventional napkin designs is the distance between the point in the body where the body exudate leaves and the napkin surface—the larger the distance the greater the chance of its slipping through the body surface itself and leaking.

U.S. Pat. No. 5,702,380, describes a woman's sanitary napkin provided with a longitudinal central protuberance, the protuberance being adapted to be located between the user's labia majora, but not penetrating into her vagina. The central protuberance is an element provided with several components, viz, an absorbent packing which is covered on its surface by a permeable cover layer and contains the central rod of an inverted T shaped fluid drawing device inside same. This sanitary napkin has a number of drawbacks:

the central protuberance is aligned with the rest of the napkin element, in such a way that when the napkin is moved according to the movements of the user, the protuberance is also moved and rubbed against the inner walls of the labia majora and might cause discomfort to the user;

the central protuberance is of complex construction, either in view of its integration with the napkin surface or due to the existence of the fluid drawing device inside same.

Statutory Invention Registration H1614 discloses a woman's napkin provided with two superposed adjacent absorbent structures, the first one being protuberant and approximately tubular in the longitudinal direction, the second one being planar and elongated, wherein the first one is more comfortable and smoother than the second one, so that during the use it contacts the user's labia majora, being partially inserted between then. This achievement also provides faulty aspects, as follows:

the first absorbent structure, although being adjustable, provides an apparently excessive volume to be comfortably inserted between the user's labia majora without being inconvenient;

the first absorbent structure is attached over the second absorbent structure, thus causing a movement according to the user's movement, bringing about discomfort and even pain to the user during use;

the first absorbent structure retains fluids, and therefore provides the user with a damp feeling.

BRIEF DESCRIPTION AND OBJECTS OF THE INVENTION

In view of the problems found in the state of the art, an object of the present invention is to provide a sanitary napkin provided with an elongated conveying element for the menstrual flow which is substantially disposed along a central longitudinal axis of the sanitary napkin.

Another object of the present invention is a sanitary napkin cooperating with the user's vulva area in order to collect and convey the flow of vaginal exudates to the central area of the absorbent pad surface, thus minimizing the possibilities of leakage due to the early displacement of the exudates towards the sides of the article.

Still another object of the present invention is a sanitary napkin provided with a conveying element for the menstrual flow that during the use penetrates at less partially between the user's labia majora in a less aggressive way and almost not subject to the movement of the user's body.

Such objectives are reached by a sanitary napkin characterized by being comprised an element that is capable of collecting and conveying vaginal exudates to an absorbent element, the conveying element being substantially laminar and oriented in a position that is orthogonal to the surface of the sanitary napkin.

Concisely, some aspects of the invention are the collection of the vaginal exudate, the conveyance of the exudate to the absorbent element and the cooperation of the sanitary napkin with the user's vulva area.

Within a particular embodiment of the present invention, the conveying element for vaginal exudates (blood, urine, inter-menstrual secretions, and the like.) is embodied as a non-woven fabric veil preferably joined only to the ends of the sanitary napkin by attachment points substantially disposed along the central longitudinal axis of the sanitary napkin. When put in use, the sanitary napkin assumes longitudinally arcuate configuration following the anatomy of that area of the body, thus orthogonally suspending the conveying element in relation to the surface of the sanitary napkin. In that position, during the use, the conveying element penetrates, even partially, between the user's labia majora, thus urging any exudate discharge to contact and follow the surface of the-conveying element as far as the central area of the sanitary napkin surface. The leakage trend due to discharges of exudates close to the sanitary napkin edges, mainly the most voluminous ones, is thus prevented, since the conveying element conveys the exudate flow to the center of the absorbent pad—the effect is theoretically compared to that attained in a chemistry laboratory, wherein a liquid to be poured inside a beaker flows down a glass rod. Additionally, since the conveying element is sufficiently thin and delicate, the drawback found in prior art products that propitiate the partial insertion of an appendix of the sanitary napkin between the user's labia majora is greatly reduced.

In a preferred embodiment, the conveying element of the sanitary napkin of the invention is equidistantly located with respect to the side edges.

Although not essential, the resiliency of at least the edge of the conveying element (which edge is adapted to contact the user's vaginal area in use) facilitates its orthogonal positioning in relation to the surface of the absorbent element, and consequently its ability to be inserted in the user's vaginal area.

The conveying element of the sanitary napkin is vertically aligned with the absorbent element and affixed to a top layer of the sanitary napkin by a curtain portion that permits independent movement of the absorbent element and the laminar collecting device that may be caused by the movement of the user's body. Thus, the absorbent element is not integrally or substantially affixed to the body contacting surface of the conveying element. That is, the conveying element and the absorbent element are adapted to prevent the transference of the movement from one to the other - optionally, the conveying element is joined to only two points to the sanitary napkin, viz, the conveying element is adhered to the sanitary napkin in each of the two opposing longitudinal end regions, and is thus affixed only at one point from each one of the two opposing longitudinal extremities adjacent to the absorbent element.

In order to attain an optimized performance of the present invention, it is essential that the conveying element, when the absorbent of the invention is in use, extends from the area in contact with the user's vagina to the surface of the top layer of the sanitary napkin, even if it is not joined or otherwise adhered thereto. This is explained by the fact that the vaginal exudate, when contacting any portion of the conveying element, flows along the surface thereof, for example, by capillarity, the purpose of which is to reach the body facing surface of the sanitary napkin, to be absorbed and retained therein. The embodiments that favor a greater contact between the conveying element and the surface of the napkin are preferred.

As can be understood from this text, the absorbent element of the sanitary napkin comprises at least a pad of absorbent material, typically a wood pulp fiber block, but it can include other components (such as superabsorbent substrata, other types of fibers and materials, etc.) also in distinct layers (for example, a non-woven layer or perforated plastic film located on the absorbent material itself to contact the user's body, etc.).

The conveying element can be comprised of one or more layers of a same material or distinct materials. The preferred material is a non-woven fabric, however other conventional flexible materials that are used to manufacture disposable sanitary products, for example, tissue, plastic film, paper, etc. may be used to form the conveying element. The conveying element is preferably configured to be able to penetrate between the user's labia majora, or to simply contact them externally. Accordingly, the conveying element preferably has a thickness less than 5 mm, preferably less than 2 mm. Its surface can be continuous or discontinuous, surfaces having orifices or discontinuities with round, square shaped forms, or of any another format being within the scope of the invention. Also within the scope of the invention, configurations of the conveying element comprise:

- a set of filaments which are spaced apart and/or parallel, with little or no interconnection transverse to the direction of the descending movement of the fluid to be conveyed;
- a corrugated laminar material, of one or more layers associated with one another;
- an arrangement where two or more layers are associated with one another thus forming tubular passages generically parallel to the direction of the descending movement of the fluid to be conveyed.

The conveying element can be hydrophobic, hydrophilic, or concomitantly contain independent portions of opposing hydrophilic and hydrophobic character. The affinity for the aqueous medium can be of the material per se or acquired through some treatment or coating.

The conveying element can optionally contain an absorbent material and/or may be provided with embossed lines or embossed areas, that have been compressed to a greater degree than the material adjacent thereto, in such a way that it affects the speed of liquid distribution.

BRIEF DESCRIPTION OF THE DRAWINGS

The present invention will be described in full details below based on a practical example represented in the accompanying drawings. The respective figures show.

DETAILED DESCRIPTION OF THE FIGURES

Figure 1:
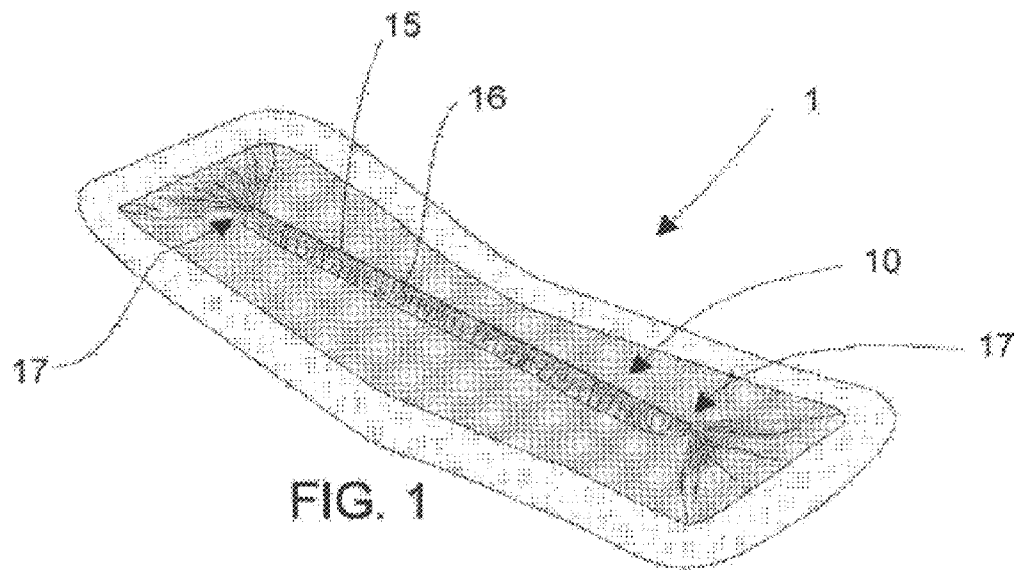
FIG. 1—a perspective view of a preferred embodiment of the sanitary napkin made in accordance with the present invention.

The sanitary napkin 1 of the present invention is comprised of an elongated absorbent core 6, wrapped by a top layer 3 and a lining layer 4.

The top layer 3 contacts the pelvic area of the user and usually is made of liquid previous material that does not cause any irritation to the user's skin, for example, non-woven or perforated plastic film.

The purpose of the lining layer 4, opposite the top layer, is to prevent the fluid retained in the absorbent core from passing to the user's clothes and usually is a thin film made of liquid impervious material, for example, polyethylene.

According to the present invention, the napkin 1 is provided with a substantially straight and elongated conveying element 10 that is capable of conveying and collecting liquids. The conveying element 10 is disposed on a body faceable side of the top layer 3 and extends substantially along a central longitudinal axis of the napkin 1. According to a particular embodiment, the element 10 extends along a longitudinal length corresponding to ⅔ of the length of the napkin 1, but it can extend along the entire length, or extend along shorter lengths, for example less than the half of the length of the napkin 1.

Still according to a preferred embodiment, the conveying element 10 comprises a longitudinally extending main portion 15 and a curtain portion 15. The main portion is adapted to contact a wearer's body when in use and is preferably elastic (for example, due to the presence of an elastic thread 14), that extends between the two main attachment points 17 to the element 10 of the napkin 1. The curtain portion 16 vertically extends from the main portion 15 to the top layer 3 of the napkin 1 along the entire length of the conveying element 10. The curtain portion 16 can be continuous along the entire length of the main portion 15 or alternatively it may be discontinuous, for example, through a plurality of orifices (not shown) perpendicular to the longitudinal axis. Depending on its efficiency, the size of the curtain portion 16 can be reduced.

The attachment points 17 are preferably provided by joining (i.e., any process known to the skilled artisan such as sewing, ultrasonic sealing, adhesives, and the like) the main portion 15 to the napkin 1. As shown in the Figures, the attachment points preferably join the main portion 15 to top layer 3 of the napkin 1. However, the ends of the main portion 15 may alternatively be joined to any other outer surfaces of the napkin 1, such as, for example, the lining layer 4.

The main portion 15 and the curtain portion 16 may be made of absorbent, hydrophilic or hydrophobic materials. Preferably, the material is a non-woven fabric, a perforated plastic film or non-perforated plastic film, a laminate of a nonwoven fabric and a layer of tissue, a laminate of a perforated plastic film and a layer of tissue or combinations thereof.

The main portion 15 and the curtain portion 16 of the element 10 according to this invention may optionally be configured as an orthogonal continuation of the top layer 3 of the sanitary napkin 1 itself. In accordance with this embodiment, the top layer 3 extends across an upper surface of the sanitary napkin and is folded over one or more strands of a longitudinally extending elastic strip. The longitudinally extending elastic strip is vertically displaced above the upper surface of the napkin. The cover layer 3 is in contact with the subjacent absorbent core 6 from the longitudinal side edges inward to a central region of the napkin whereupon the cover layer is folded vertically away from the absorbent core 6, folded over the main portion 15 and then downward to again contact the absorbent core 6 from the center region to the opposite longitudinal side edge. Thus, the curtain portion 16 of the element 10 is formed from a two layer laminate of top layer 3. In a preferred embodiment, the two layer laminate structure for the curtain portion 16 is adhesively secured together along at least a portion of the curtain portion 16. In a most preferred embodiment, the folded portion of the top layer 3 in the main portion 15 is substantially free of adhesive to form a cavity for the elastic strip.

The main portion 15 also can be made of a non-elastic material. In accordance with this embodiment, its length will be preferably shorter than the corresponding longitudinal length of the napkin 1, so that the main portion 15 can be stretched and moved away from the corresponding longitudinal length of the top layer 3 of the napkin 1 when the latter is opened or unfolded, thus facilitating the formation of the straight portion of use illustrated in FIG. 1.

The main portion 15 is preferably conformed as a elongated strip that represents a prolongation of the curtain portion 16. In an alternative embodiment, the main portion 15 may be formed from two or more curtain portions 16. The main portion 15 can alternatively be formed as an elongated strip disposed perpendicular to the curtain portion 16 (see FIG. 3), or still as a channel member having a V cross-section (see FIG. 4) or a "U" cross-section (see FIG. 5). An alternative similar to that of FIG. 4 or 5 is not illustrated where the main portion 15 is planar and not as a channel member.

Figure 2:
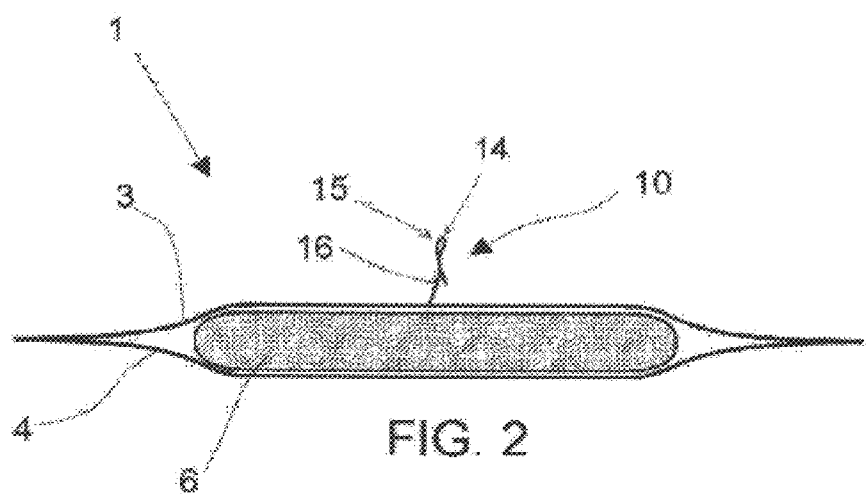
FIG. 2—a cut view of the napkin illustrated in FIG. 1.
Figure 3:
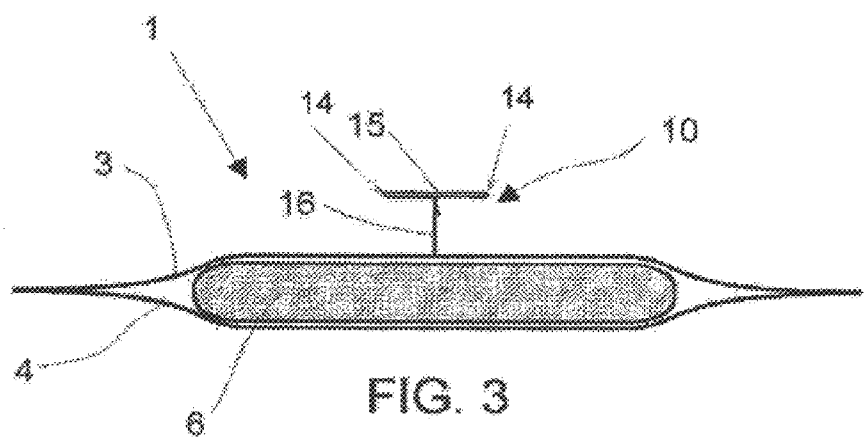
FIG. 3—a cut view of a variation of the preferred embodiment of the napkin illustrated in the figures above.
Figure 4:
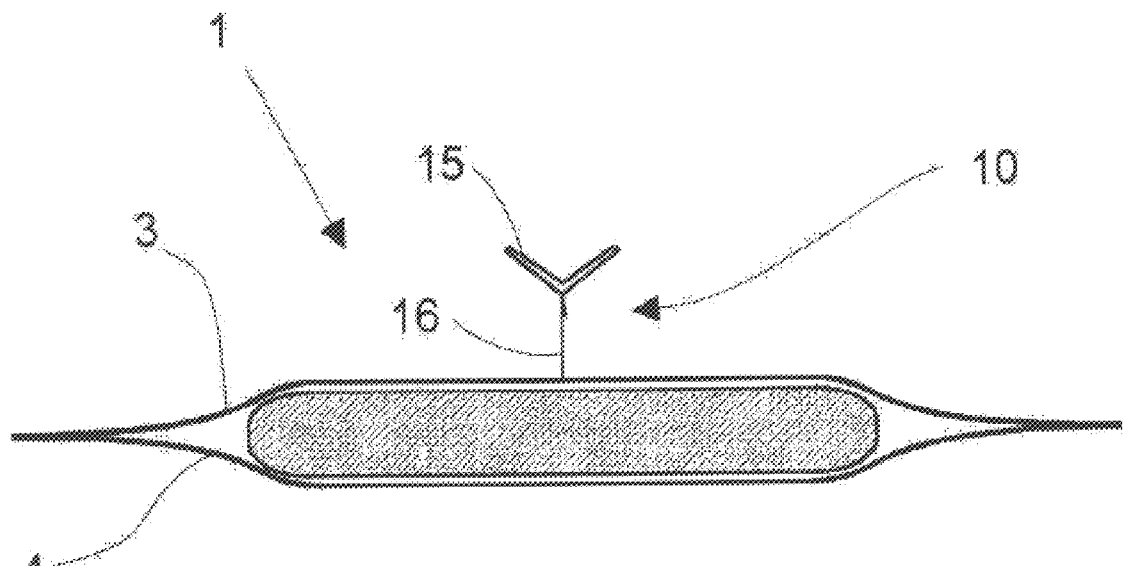
FIG. 4—a cut view of a second embodiment of the napkin in question.
Figure 5:
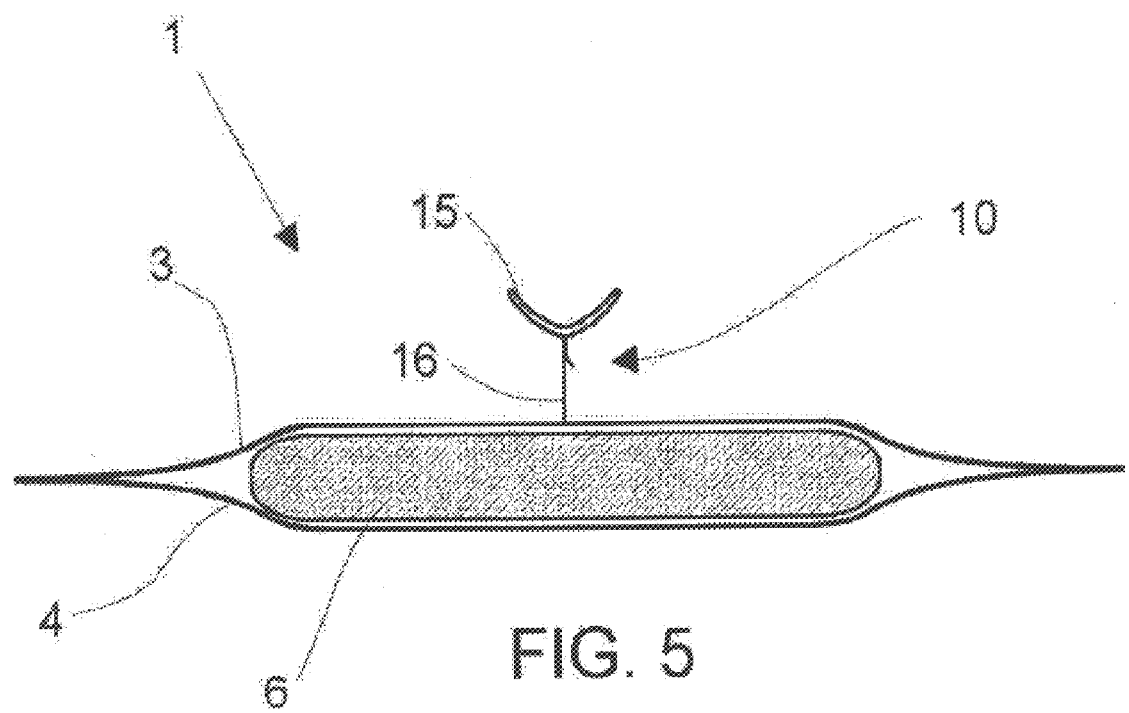
FIG. 5—a cut view of a third variation of the napkin in question.

In the embodiments illustrated in FIGS. 1 and 2, the main portion 15, during the use, is adapted to be partially inserted between the user's labia majora, while in the embodiments of FIGS. 3, 4 and 5 the main portion has a wider external contact with the user's genitalia.

In the presence of the curtain portion 16, firstly the vaginal exudate contacts the main portion 15 of the conveying element 10, and is conveyed later (through the surface tension, capillarity, and the like) by the curtain portion 16 towards the top layer 3 of the napkin 1. Thus, the fluid is advantageously conveyed to a central area of the napkin which is capable to withstand larger fluid discharges than the peripheral areas of the napkin 1 without any leakage. Thus, the possibility of leakage is considerably mitigated.

It is not essential that the curtain portion 16, beyond the attachment points 17, be joined through sealing, gluing or any other method, to the surface of the absorbent element, in this example embodied by the top layer 3—most importantly, a physical proximity between the portion 16 and the top layer 3 is required so that the fluid can be transferred to and stored in the absorbent core 6.

An optional embodiment (not shown) comprises a main portion 15 including an upward bending in its longitudinal medium portion orthogonal to the surface of the napkin 1, so that it has an increased penetration in the user's vulva area, thus incrementing the advantages of this invention.

After the examples of the preferred embodiments have been described, it should be understood that the scope of the present invention embodies other possible variants, being limited only by the text of the accompanying claims, the possible equivalents being included thereto.

What is claimed is:

1. A sanitary napkin comprising a top layer, a lining layer and an absorbent core, the absorbent core being disposed between the top layer and the lining layer, and a conveying element being associated with the top layer and vertically aligned along a central longitudinal axis of the sanitary napkin, the conveying element being substantially laminar and orthogonal to the surface of the napkin and having a main portion and a curtain portion, wherein the main portion, during the use, is adapted to be partially inserted between a user's labia majora.

2. The sanitary napkin in accordance with claim 1 wherein the conveying element is associated with the top layer by attachment points located in extreme and opposing points of the longitudinal axis of the napkin.

3. The sanitary napkin in accordance with claim 1 wherein the conveying element is an orthogonally extending prolongation of the top layer.

4. The sanitary napkin in accordance with claim 2, wherein the attachment points are located along the longitudinal axis of the napkin.

5. The sanitary napkin in accordance with claim 1 wherein the main portion is substantially parallel with the top layer and is vertically spaced apart from the top layer along at least a portion of the conveying element, the curtain portion being substantially orthogonal to the top layer and extending from the main portion to the top layer along the entire longitudinal length of the sanitary napkin.

6. The sanitary napkin in accordance with claim 1, wherein the conveying element is at least partially formed from an elastic material.

7. The sanitary napkin in accordance with claim 1, wherein the conveying element is at least partially made of a non-woven material.

8. The sanitary napkin in accordance with claim 5, wherein the curtain portion is continuous.

9. The sanitary napkin in accordance with claim 5, wherein the curtain portion is discontinuous.

10. The sanitary napkin in accordance with claim 5, wherein the main portion and/or the curtain portion are made of absorbent material.

11. The sanitary napkin in accordance with claim 5, wherein the main portion and/or the curtain portion are made of a non-absorbent material.

12. The sanitary napkin in accordance with claim 5, wherein the main portion is configured with an elongated strap that is a prolongation of the curtain portion, or else is disposed perpendicular to the curtain portion.

13. A sanitary napkin comprising a top layer, a lining layer and an absorbent core, the absorbent core being disposed between the top layer and the lining layer, and a conveying element being associated with the top layer and vertically aligned along a central longitudinal axis of the sanitary napkin, the conveying element being substantially laminar and orthogonal to the surface of the napkin and consequently its ability to be inserted in the user's vaginal area wherein the main portion is substantially parallel with the top layer and is vertically spaced apart from the top layer along at least a portion of the conveying element, the curtain portion being substantially orthogonal to the top layer and extending from the main portion to the top layer along the entire longitudinal length of the sanitary napkin wherein the main portion has a V-shaped or U-shaped cross-section which is disposed perpendicular to the curtain portion.

14. The sanitary napkin in accordance with claim 5 wherein the curtain portion of the conveying element is at least partially joined to the top layer.

15. The sanitary napkin in accordance with claim 1, wherein the conveying element has a thickness less than 5 mm.

16. The sanitary napkin in accordance with claim 1, wherein the conveying element has a longitudinal length of approximately ⅔ of the longitudinal length of the absorbent element.

17. The sanitary napkin in accordance with claim 1, wherein the conveying element has a thickness less than 2 mm.

* * * * *